United States Patent
Bonnadier et al.

(10) Patent No.: US 10,532,152 B2
(45) Date of Patent: Jan. 14, 2020

(54) NEEDLES MADE OF A PARTICULAR PLASTIC MATERIAL

(75) Inventors: Jean-Baptiste Bonnadier, Bollate MI (IT); Daniel J. Ireland, Kernersville, NC (US); Henri Massillon, Waremme (BE)

(73) Assignee: SOLVAY SPECIALTY POLYMERS USA, L.L.C., Alpharetta, GA (US)

( * ) Notice: Subject to any disclaimer, the term of this patent is extended or adjusted under 35 U.S.C. 154(b) by 855 days.

(21) Appl. No.: 13/634,645

(22) PCT Filed: Mar. 16, 2011

(86) PCT No.: PCT/EP2011/053982
§ 371 (c)(1),
(2), (4) Date: Sep. 13, 2012

(87) PCT Pub. No.: WO2011/113865
PCT Pub. Date: Sep. 22, 2011

(65) Prior Publication Data
US 2013/0030390 A1      Jan. 31, 2013

Related U.S. Application Data (60) Provisional application No. 61/314,613, filed on Mar. 17, 2010.

(30) Foreign Application Priority Data

Mar. 29, 2010  (EP) .................................... 10158123
May 11, 2010   (EP) .................................... 10162490

(51) Int. Cl.
*A61M 5/00*     (2006.01)
*A61B 17/06*    (2006.01)
(Continued)

(52) U.S. Cl.
CPC .............. *A61M 5/158* (2013.01); *A61M 5/32* (2013.01); *A61M 5/3286* (2013.01); *C08L 65/00* (2013.01);
(Continued)

(58) Field of Classification Search
CPC ...... A61M 5/00; A61M 5/158; A61M 5/3286; A61M 5/32; A61B 17/06; C08L 65/00;
(Continued)

(56) References Cited

U.S. PATENT DOCUMENTS 4,617,019 A * 10/1986 Fecht .................. A61M 25/001
                                                          604/274
5,151,231 A    9/1992 Lambert et al.
(Continued)

FOREIGN PATENT DOCUMENTS

EP    0451184 B1 *  7/1993 .............. A61M 5/32
JP    07303700 A    11/1995
(Continued)

OTHER PUBLICATIONS

Podder, et al., "Effects of tip geometry of surgical needles: an assessment of force and deflection," The 3rd European Medical and Biological Engineering Conference, Prague, Czech Republic, Nov. 20-25, IFMBE Proc., 11(1), 2005, p. 1-4.*
(Continued)

*Primary Examiner* — Gerard Higgins
*Assistant Examiner* — Kevin C Ortman, Jr.
(74) *Attorney, Agent, or Firm* — Osha Liang LLP (57) ABSTRACT

Needle comprising a polyarylene material comprising a polyarylene. The needle can meet all the advantages of metal, while avoiding its drawbacks. It has a high rigidity and ductility, and is excellent in penetrability and ability to hold a sharp edge. It is easily disposable and recyclable. It is non toxic and non irritant.

16 Claims, 1 Drawing Sheet

(51) Int. Cl.
*A61M 5/158* (2006.01)
*C08L 71/00* (2006.01)
*A61M 5/32* (2006.01)
*C08L 65/00* (2006.01)
*C08L 81/06* (2006.01)

(52) U.S. Cl.
CPC ............... *C08L 71/00* (2013.01); *C08L 81/06* (2013.01); *C08G 2261/312* (2013.01); *C08G 2650/40* (2013.01)

(58) Field of Classification Search
CPC .......... C08L 71/00; C08L 65/02; C08L 81/06; C08G 2650/40; C08G 2261/312
USPC ................... 428/36.9, 34.7, 36.3, 35.7, 36.4; 604/272; 606/223
See application file for complete search history.

(56) References Cited

U.S. PATENT DOCUMENTS

| | | | |
|---|---|---|---|
| 5,227,457 | A | 7/1993 | Marrocco, III et al. |
| 5,539,048 | A | 7/1996 | Gagne et al. |
| 5,565,543 | A | 10/1996 | Marrocco, III et al. |
| 5,637,399 | A | 6/1997 | Yoshikawa et al. |
| 5,646,231 | A | 7/1997 | Marrocco, III et al. |
| 5,654,392 | A | 8/1997 | Marrocco, III et al. |
| 5,659,005 | A | 8/1997 | Marrocco, III et al. |
| 5,668,245 | A | 9/1997 | Marrocco, III et al. |
| 5,670,564 | A | 9/1997 | Gagne et al. |
| 5,721,335 | A | 2/1998 | Marrocco, III et al. |
| 5,756,581 | A | 5/1998 | Marrocco, III et al. |
| 5,760,131 | A | 6/1998 | Marrocco, III et al. |
| 5,824,744 | A | 10/1998 | Gagne et al. |
| 5,827,927 | A | 10/1998 | Gagne et al. |
| 5,869,592 | A | 2/1999 | Gagne et al. |
| 5,886,130 | A | 3/1999 | Trimmer et al. |
| 6,087,467 | A | 7/2000 | Marrocco, III et al. |
| 2004/0199127 | A1 | 10/2004 | Jensen et al. |
| 2007/0073249 | A1 | 3/2007 | Zambaux et al. |
| 2008/0312387 | A1 | 12/2008 | El-Hibri et al. |
| 2009/0041924 | A1 | 2/2009 | Steube |
| 2009/0069511 | A1* | 3/2009 | Thomas et al. ............... 525/471 |
| 2009/0082539 | A1 | 3/2009 | Maljkovic et al. |
| 2010/0268192 | A1* | 10/2010 | El-Hibri et al. ............. 604/511 |

FOREIGN PATENT DOCUMENTS

| | | | | |
|---|---|---|---|---|
| WO | WO 2006037078 A2 * | 4/2006 | | |
| WO | WO 2009034087 A2 * | 3/2009 | ............ | A61L 27/26 |
| WO | WO 2009053426 A2 | 4/2009 | | |

OTHER PUBLICATIONS

Webster (https://www.merriam-webster.com/dictionary/needle, p. 1-12, accessed Sep. 18, 2018) (Year: 2018).*
Weast R.C., "Definitive Rules for Nomenclature of Organic Chemistry", 1983-1984, CRC Handbook of Chemistry and Physics, 64th edition, CRC Press Inc., Boca Raton, Florida; pp. C1-C44; 44 pgs.
Randic M., "Aromaticity of Polycyclic Conjugated Hydrocarbons", 2003, Chemical Reviews, vol. 103, American Chemical Society, pp. 3449-3605; 157 pgs.

* cited by examiner

NEEDLES MADE OF A PARTICULAR PLASTIC MATERIAL

CROSS-REFERENCE TO RELATED APPLICATIONS

This application is a U.S. national stage entry under 35 U.S.C. § 371 of International Application No. PCT/EP2011/053982 filed Mar. 16, 2011, which claims priority to U.S. provisional application 61/314,613, filed Mar. 17, 2010, to EP application 10158123.9, filed on Mar. 29, 2010, to EP application 10162490.6, filed on May 11, 2010, whose disclosures are incorporated herein by reference.

FIELD OF THE INVENTION

The present invention relates to a plastic needle made of a particular polymer material. It also relates to a syringe, to a cannula-based system and to a recipient connector comprising said plastic needle. It relates also to the use of said plastic needle in a broad range of applications.

BACKGROUND OF THE INVENTION

Needles are used in a variety of applications. Medical, surgical and cosmetic needles are broadly used to penetrate into a human or animal body. Metal and metal alloys, especially stainless steel, has been for several decades the material of choice for needles.

Stainless steel needles have been appreciated for their high compression and flexural strength, high rigidity, high stiffness, high surface hardness, high ductility, high impact resistance, high chemical resistance, high corrosion resistance, non combustibility, low moisture absorption, good ability to hold a sharp edge and penetrability.

The penetrability of a needle can be defined as the ability or easiness for a needle to penetrate in a suitable manner into a substrate such as a skin or a vein; upon penetration, the needle should neither break nor endorse a substantial deformation; it should not tear up in any manner the substrate that is penetrated (esp. it should not rip up the flesh). Further, needles for injection into human or animal tissue have to be terminated by a sharp edge (also named, point) and to be very small in diameter in order to limit the pain experienced by the patient, whilst retaining adequate penetrability of the skin, vein, muscle or the like.

As the skilled person will easily understand, this property is key for a needle and is essentially specific to this end use. Insofar as the Applicant knows, it is extremely difficult to predict what the penetrability of a needle is based on more familiar properties of the material the needle is made of. Besides, without being bound to any theory, the Applicant is of the opinion that achieving the right penetrability likely requires a subtle and unelucidated balance of properties, among which it could possibly be cited a.o. high compression and flexural strength and high rigidity on one hand, and high ductility and a high impact resistance on the other hand; the penetrability depends further on the design of needle, including its length, aspect ratio and, last but not least, the sharpness of its edge.

With this regard, the ability to hold a sharp edge is another key property for a needle. Indeed, this property does not only improve the penetrability of the needle as above explained, but it also contributes as such to decrease or relieve the pain felt by a patient (or more generally by a human or an animal) when the needle penetrates and possibly goes through its skin, vein, muscle or other surface layer. As the skilled person will easily appreciate, it is also essentially specific to needle end uses. The Applicant is not aware of any study that would have addressed so far the question of the ability for a needle to hold a sharp edge as function of the chemical nature of the plastic material the needle would have been made of. Finally, to the best of the Applicant's knowledge, it is also extremely difficult to predict the ability of a needle to hold a sharp edge, relying on more familiar properties of the material the needle is made of. Finally, without being bound to any theory, the Applicant is of the opinion that the ability for a needle to hold a sharp edge likely requires a complex and obscure balance of properties, among which it could possibly be cited a.o. a high compression and flexural strength and a high rigidity on one hand, and a high stiffness and a high surface hardness on the other hand; it depends further on the machinability of the material the needle is made of, in particular of the melt processability of the plastic material in case of plastic needles.

Because of this confluence of properties, the needles of the prior art have been generally made of metal. However, metal needles, once they have been used, cannot be easily disposed of, and this gives rise to a sanitary health problem because of contamination accidents arising from contact with or accidental re-utilization of thereof. Indeed, while a needle, such as a medical, surgical or cosmetic needle, can be manufactured under sterile and apyrogenic conditions, and can be kept sterile and apyrogenic in its original pack, once it has been taken out from its pack and utilized, it cannot obviously be held anymore as sterile and apyrogenic.

There is a strong need for single-use, easily disposable needles. This need is immediately apparent when thinking about applications such as mass vaccinations in Third-World countries which are not or poorly equipped with facilities allowing for re-sterilizing or depyrogenizing hypodermic needles that have already been used. Also, even in countries equipped with such facilities, re-sterilization and depyrogenization remain a tedious, time-consuming and complex processes, and, in general, it is also difficult to find reconditioning installations that would provide the same level of health safety as high as those offered by those achieving the original conditioning of the needles.

Another problem commonly associated with metal needles results in the rather poor machinability of the metal, which problem is particularly acute when needles terminated by an extremely sharp edge have to be machined, as required by certain applications in the medical field or as it is the case with single tattoo needles.

There is thus also a need for needles which can be machined more easily, including when the needles have an extremely sharp edge.

In order to solve the problem of providing single-use, easily disposable, easily machinable needles suitable for penetrating into the human body and able to hold a sharp edge, needles made of certain plastic materials have been proposed.

JP 7 303 700, the whole content of which is herein incorporated by reference for all purposes, describes a synthetic resin needle reinforced with combustible fibers whose longitudinal directions are arrayed straight or curvilinearly along the axial length of the needle. JP'700 proposes a wide variety of resins for making the reinforced synthetic needle. According to JP'700, the resin can be notably a thermoplastic resin, such as a polyphenylene sulfide, a polyetheretherketone, a polybutyleneterephthalate, a polycarbonate, a polyamide, a polyacetal, a modified polyphenylene ether, a polyester system resin, a polytetrafluoroethylene, a fluororesin, a polysulfone, a polyetherimide, a polyethersulfone, a polyetherketone, a polyetherlactone, a liquid crystal polyester, a polyamideimide, a polyimide or a polyethernitrile, a polypropylene, a polyethylene or a cyclic olefin system resin; it can also be a thermoset resin such as an epoxy resin, an unsaturated polyester resin, a phenol resin, a urea resin, a melamine resin or a polyurethane resin.

US 2004/199127, the whole content of which is herein incorporated by reference, describes a process for the manufacture of a plastic injection needle in which the employed plastic is a liquid crystalline polyester comprising 70-80 percent hydroxybenzoic acid and 20-30 percent hydroxynaphthoic acid. The plastic needle of US 2004/199127 preferably further comprises from 15 to 40 percent by weight of the solid plastic of fiber reinforcement such as glass fiber or carbon fiber or aramid fiber.

While easily disposable, the needles U.S. Pat. No. '127 which are made of unreinforced liquid crystalline polyester have not the suitable confluence of properties achieved by metal needles, lacking notably in compression and flexural strength, rigidity, penetrability and ability to hold a sharp edge. By the way, exactly the same drawbacks would apply to needles that would have been made of unreinforced polymer material based on any of the synthetic resins described in JP'700, in particular based on polyetheretherketone (PEEK).

Likewise, the needles U.S. Pat. No. '127 which are made of reinforced liquid crystalline polyester and, more generally, the needles of JP'700 which can be made of a variety of other reinforced synthetic resins, have not the suitable confluence of properties achieved by metal needles, lacking notably in ductility, impact resistance, penetrability and ability to hold a sharp edge; the reinforcing agent present in the synthetic resin matrix limits also substantially the possibilities of subsequent recycling of the polyester material.

US 2007/073249, the whole content of which is herein incorporated by reference, describes a needle constituted of a cylindrical body extended along a longitudinal axis, said body being made of a polyaryletherketone polymer (such as PEEK) and further comprising metal reinforcement wires embedded in the polyaryletherketone polymer, extending parallel to the longitudinal axis and distributed according to a particular design. The composite needle of U.S. Pat. No. '249 is not easily disposable because of the metal reinforcement wires embedded in the polymer matrix. The composite needle of U.S. Pat. No. '249 is more difficult to manufacture than a simple plastic or a metal needle. In addition, meeting a suitable confluence of properties with such a composite needle requires also more subtle adjustments, depending further notably on amount, dimensions, shape and positioning of the metal wires.

There are still other reasons making it extremely difficult to find a plastic material that could suitably replace metal for numbers of needle applications.

Firstly, needles are typically small in diameter, and hollow needles have typically very thin walls, which can makes it difficult to mold a plastic material in a standard mold, or to extrude a plastic material through a standard extrusion head/die. Oftentimes, the viscosity of these materials in the die is so high that one must increase the temperature of the polymer in order to reduce the viscosity of the material so that they can get sufficient flow in the orifices of the mold or through the die. This practice can dramatically alter material properties. Hence, plastic materials suitable for making needles must demonstrate a good thermal stability and good melt processability.

Then, needles used to penetrate into a human or animal body, must be non toxic and non irritant. They should not elicit any adverse host reactions to their contact, and, more generally, they should cause no injurious effect on the part of the body the are put in contact with. This further requires the plastic material to demonstrate excellent biocompatibility features.

There is a need for needles, in particular medical and surgical needles, exhibiting a confluence of characteristics including high compression and flexural strength, high rigidity, high stiffness, high surface hardness, high ductility, high impact resistance, high chemical resistance, high corrosion resistance, non combustibility, low moisture absorption.

There is a need for needles having a good penetrability.

There is a need for needles having a good ability to hold a sharp edge.

There is a need for needles that are non toxic. There is a need for needles that are non irritant. There is a need for needles that are biocompatible.

There is a need for easily disposable needles, which would then be especially well suited for a single-use. There is a need for needles made from a material exhibiting a good disposability and recyclability.

There is a need for needles made from an easily machinable material. There is a need for needles made of an easily melt processable and thermally stable material.

The present invention can solve the above problems.

SUMMARY OF THE INVENTION

The present invention concerns a needle (N) comprising a body extending along a longitudinal axis and having two ends, wherein at least one end of the body is beveled and wherein the body comprises a polyarylene material (M) comprising at least one polyarylene (P).

BRIEF DESCRIPTION OF THE DRAWING

For a detailed description of preferred embodiments of the invention, reference will now be made to the accompanying drawing, in which FIG. 1 illustrate several embodiments in which at least one bevel terminating the body of a needle) N) is a standard, short or true short bevel.

DETAILED DESCRIPTION OF THE INVENTION

The Needle (N)

The needle (N) is typically a sharp pointed, slender instrument.

The needle (N) of the present invention is of particular interest when it is designed (and possibly, used) for the prevention, cure, alleviation, or correction of diseases, injuries, irregularities, disorders and deformities of any part of a human or animal body. The needle can be designed for use (and possibly, used) in non operative procedures (e.g. within the frame of a medical or dental therapy) or in operative procedures (e.g. within the surgical operation).

In certain preferred embodiments of the present invention, the needle (N) is a medical needle. For the purpose of the present invention, a "medical needle" is intended to denote a hollow needle designed to (and possibly, used to) introduce a material into or remove a material from a human or animal body, in general parenterally (e.g. intravenously, intramuscularly, or subcutaneously). The medical needle is commonly designed to be used (and is commonly used) attached to a syringe; the material can be injected or aspired.

In certain very preferred embodiments of the present invention, the needle (N) is a hypodermic needle. A hypodermic needle is a medical needle designed (and possibly, used) to introduce or remove from a human or animal body a material subcutaneously. It can be designed (and possibly, be used) to inject a liquid into the body. It can also be designed (and possibly, used) to take liquid samples from the body, for example taking blood from a vein in venipuncture. Large bore hypodermic intervention using a suitably designed hypodermic needle is especially useful in catastrophic blood loss or shock. A suitably designed hypodermic needle can also be used for rapid delivery of liquids, or when the injected substance cannot be ingested, either because it would not be absorbed (as with insulin), or because it would harm the liver. There are many possible routes for an injection, and it is further understood that the medical needle as herein broadly defined can be useful not only in non operative procedures, but also in operative ones. Hypodermic needles are usually used by medical professionals (physicians, nurses, paramedics), but they are sometimes used by patients themselves; this is common notably with certain diabetics who may require several insulin injections a day.

Figure 1:
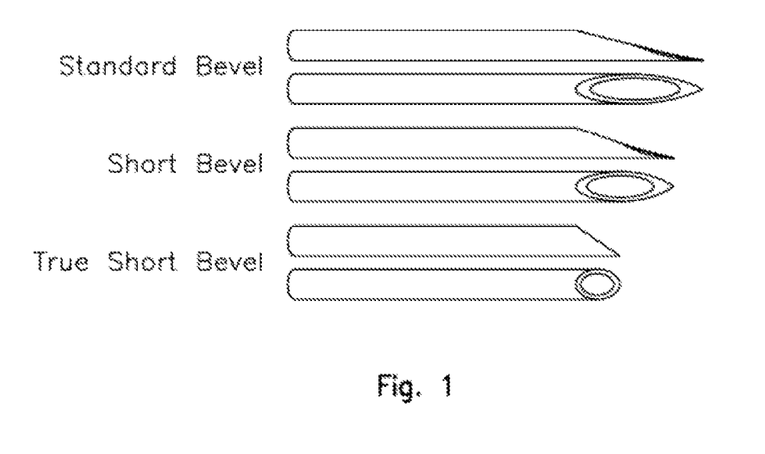

In other preferred embodiments of the present invention, the needle (N) is a reconstitution needle. A reconstitution needle is designed (and possibly used) to penetrate a first sealed vial containing a first material through its seal (e.g. rubber stopper or other cap), then drawing up the first material into a syringe for mixing or injecting into a second sealed vial, etc. The reconstitution needle is particularly useful for medical applications, e.g. for mixing drugs or for diluting concentrated or lyophilized drugs in a diluent; once a desired drug is finally obtained, the reconstitution needle is removed from the syringe, and a traditional hypodermic needle is then generally used for injecting the final material into the body of a human or animal patient. The reconstitution needle is also useful for cosmetic applications like for reconstituting a neurotoxin solution, e.g. for drawing up in a syringe a proper amount of a saline contained in a first vial then inserting and injecting this amount of saline in a second vial containing a vacuum-dried neurotoxin such as onabotulinumtoxin A; then, the reconstitution needle is removed from the syringe, and a traditional hypodermic needle is then generally used for the injection the neurotoxin-contg. solution into the muscles of a human.

In other embodiments of the present invention, the needle (N) is an acupuncture needle, which is designed to be (and possibly, is) inserted at specific points through the skin of a human or animal body, especially for the purpose of curing disease or other symptoms, or for relieving or controlling pain (as during a surgical operation).

In other embodiments of the present invention, the needle (N) is a surgical needle. For the purpose of the present invention, a surgical needle is intended to denote a needle designed (and possibly, used) to carry sutures on a tissue, to puncture a tissue or to pass a ligature on a conduit of a human or animal body. For example, the surgical needle can be designed respectively to carry sutures on a tissue during a surgery, to puncture a skin, to pass a ligature around an artery. It is understood that the medical needle as herein broadly defined can be useful not only in operative procedures, but also in non operative ones.

In still other embodiments of the present invention, the needle (N) is a cosmetic needle. For the purpose of the present invention, a cosmetic needle is intended to denote a needle designed for (and possibly, used in) a treatment tending to beautify, to preserve, restore or confer comeliness, to improve the appearance of a physical feature, irregularity or defect of a human or animal body. A cosmetic needle can be useful for injecting collagen.

In still other embodiments of the present invention, the needle (N) is designed (and possibly, used) to modify the external appearance of the skin of a human body. As an example thereof, it can be cited a piercing needle, a single tattoo needle (for fine lining), and those needles called sharps attached to a tattoo needle bar.

Usually, the needle (N) consists essentially of, or even consists of the body extending along a longitudinal axis and having two ends. However, additional bodies may be present, especially in unconventional needles such as tattoo needles which may be linked together by a bar. The body extending along a longitudinal axis and having two ends of the needle (N) can represent more than 50 wt. %, more than 75 wt. %, more than 90 wt. %, more than 95 wt. %, more than 99 wt. %, up to 100 wt. % of the total weight of the needle (N). Unless otherwise specified, whenever the terms "the body of the needle (N)" are used within the present specification, they are intended to designate the body extending along a longitudinal axis and having two ends, which is the only essential body of the presently invented needle.

The body of the needle (N) is advantageously essentially cylindrical. Preferably, it is cylindrical.

The body of the needle (N) can be extended along a straight, curving or bent, continuous or discontinuous, longitudinal axis. In preferred embodiments of the present invention, the body of the needle (N) is extended along a straight, continuous longitudinal axis.

In preferred embodiments of the present invention, the body of the needle (N) can have a hollow section all along its longitudinal axis. The hollow section of the body allows for the transportation of material, typically a liquid. The hollow section of the body is not particularly limited in shape; it can be polygonal, essentially elliptic or essentially circular; preferably, it is circular.

In other embodiments of the present invention, the body of the needle (N) has a plain section extending along more than 50% of the length of its longitudinal axis. In this embodiment, the body of the needle (N) quite often has a plain section extending along more than 90% of the length of its longitudinal axis; often, the plain section extends all along the length of its longitudinal axis. When the body of the needle (N) in accordance with the present embodiment is beveled at one and only one end, the other end may comprise or be an eye suitable for fixing a surgical thread.

The body of the needle (N) has two ends. In preferred embodiments of the present invention, the body of the needle (N) is beveled at one and only one end. In other embodiments of the invention, as will be detailed hereinafter, the body is beveled at both ends. The shape of the at least one beveled end [or bevel] is not particularly limited; examples of certain standard, short and true short bevels suitable for terminating the body of the needle (N), such as a hypodermic needle, are illustrated in FIG. 1. The acuteness of the bevel can be related to the angle $\alpha$ which the longitudinal axis of the body makes with the bevel (more precisely, with the plane incorporating the oblique surface of the bevel). $\alpha$ ranges generally from 2.5° to 60°. $\alpha$ can be of at most 45°, at most 35°, at most 25°, at most 20° or at most 15°; besides, $\alpha$ can be of at least 3.0°, at least 4.0°, at least 5.0°, at least 6.0°, at least 7.0°, at least 8.0°, at least 9.0°, at least 10°, at least 12°, at least 15°, at least 20°, at least 25° or at least 30°. α can be in any range delimited by any of the previously cited lower and upper limits, and can thus range notably from 3.0° to 45°, from 3.0° to 30°, from 3.0° to 20°, from 3.0° to 15°, from 5.0° to 45°, from 5.0° to 30°, from 5.0 to 20°, from 5.0° to 15°, from 7.0° to 45°, from 7.0° to 30°, from 7.0° to 20°, from 7.0° to 15°, from 9.0 to 45°, from 9.0° to 30°, from 9.0° to 20° or from 9.0 to 15°. In particular, the at least one bevel terminating the body of the needle (N) can be a standard bevel, substantially as shown on FIG. 1; it can be a short bevel, substantially as shown on FIG. 1; it can also be a true short bevel, substantially as shown on FIG. 1.

In certain preferred embodiments of the present invention, the body of the needle (N) is essentially composed of, or is even composed of, the polyarylene material. Very preferably, the needle (N) is essentially composed of, or is even composed of, the polyarylene material.

In other preferred embodiments of the invention, the needle is essentially free, or is even free, of reinforcement filaments embedded in the polyarylene material, such as stainless steel reinforcement filaments. In other preferred embodiments of the invention, the needle is essentially free, or is even free, of any metal or metal alloy.

Good results are obtained notably when the needle (N) consists essentially of the body, said body being essentially cylindrical, said body having an essentially circular hollow section, said body being beveled at one and only one end, and said body being essentially composed of the polyarylene material. Good results are also obtained when the needle (N) consists of the body, said body being cylindrical, said body having a circular hollow section all along its longitudinal axis, said body being beveled at one and only one end, and said body being composed of the polyarylene material.

In certain non preferred embodiments of the invention, the body of the needle (N) is a "composite body". Typically, a composite body comprises at least one structural part in addition to the polyarylene material, separated therefrom but connected thereto. The additional structural part can be in the form of filaments, such as stainless steel reinforcement filaments. A particular needle (N) in accordance with the present invention comprises a body extending along a longitudinal axis and having two ends, wherein the body consists essentially (or even, consists) of the polyarylene material and of stainless steel reinforcement filaments embedded in the polyarylene material and extending parallel to the longitudinal axis.

The needle (N), whatever its body has hollow or plain section along its longitudinal axis, can be characterized by its length (L) and its diameter or outer diameter (OD). In addition, when the body of the needle has a hollow section partially or all along its longitudinal axis, it can be further characterized by its inner diameter (ID) and wall thickness (WT).

The length of the needle (N) is generally of at most 300 mm, very often of at most 200 mm, often of at most 100 mm. It may be of at most 70 mm, at most 40 mm, at most 30 mm, at most 20 mm, at most 15 mm, at most 10 mm or at most 5.0 mm. Besides, the length of the needle (N) is generally of at least 1.0 mm, very often of at least 2.0 mm, often of at least 3.0 mm. It may be of at least 5.0 mm, at least 10 mm, at least 15 mm, at least 20 mm, at least 30 mm, at least 40 mm or at least 70 mm.

The outer diameter (OD) of the needle (N) is generally of at most 20 mm, very often of at most 10 mm, often of at most 5.0 mm. It may be of at most 4.0 mm, at most 3.0 mm, at most 2.0 mm, at most 1.5 mm, at most 1.0 mm, at most 0.80 mm, at most 0.60 mm, at most 0.40 mm, at most 0.30 mm or at most 0.20 mm. Besides, the outer diameter (OD) of the needle (N) is generally of at least 0.05 mm, very often of at least 0.10 mm, often of at least 0.15 mm. It may be of at least 0.20 mm, at least 0.30 mm, at least 0.40 mm, at least 0.60 mm, at least 0.80 mm, at least 1.0 mm, at least 1.5 mm, at least 2.0 mm or at least 3.0 mm.

When the body of the needle has a hollow section extending partially or all along its longitudinal axis, the inner diameter (ID) of the needle (N) is generally of at most 12 mm, very often of at most 8.0 mm, often of at most 4.0 mm. It may be of at most 3.0 mm, at most 2.0 mm, at most 1.5 mm, at most 1.0 mm, at most 0.80 mm, at most 0.60 mm, at most 0.40 mm, at most 0.30 mm, at most 0.20 mm or at most 0.15 mm. Besides, the inner diameter (OD) of the needle (N) is generally of at least 0.015 mm, very often of at least 0.030 mm, often of at least 0.060 mm. It may be of at least 0.080 mm, at least 0.15 mm, at least 0.20 mm, at least 0.25 mm, at least 0.30 mm, at least 0.40 mm, at least 0.60 mm, at least 0.80 mm, at least 1.0 mm, at least 1.5 mm, at least 2.0 mm or at least 3.0 mm.

When the body of the needle has a hollow section extending partially or all along its longitudinal axis, the wall thickness (WT) of the needle (N) is generally of at most 5.0 mm, very often of at most 2.5 mm, often of at most 0.50 mm. It may be of at most 0.40 mm, at most 0.30 mm, at most 0.20 mm, at most 0.15 mm, at most 0.10 mm or at most 0.080 mm. Besides, the wall thickness (WT) of the needle (N) is generally of at least 0.01 mm, very often of at least 0.02 mm, often of at least 0.03 mm. It may be of at least 0.040 mm, at least 0.060 mm at least 0.080 mm, at least 0.10 mm, at least 0.15 mm, at least 0.20 mm or at least 0.30 mm.

When the needle (N) is cylindrical, the outer diameter (OD) is calculated as the equivalent circular diameter, i.e. the diameter of the circle of equal area to that of the area of the outer cross-section. When the needle (N) has a non circular hollow cross-section, the inner diameter (ID) is calculated as the equivalent circular diameter, i.e. the diameter of the circle of equal area to that of the area of the inner cross-section. When the walls of the needle (N) do not form a circular crown, the wall thickness (WT) is calculated as the equivalent circular crown diameter.

The diameter of a medical needle, especially a hypodermic needle, is typically indicated by the needle gauge. Various needle lengths are available for any given gauge. There are a number of systems for gauging needles, including the Stubs Needle Gauge and the French Catheter Scale. Needles in common medical use range from 7 gauge (the largest) to 33 (the smallest) on the Stubs scale. Twenty-one-gauge needles are most commonly used for drawing blood for testing purposes, and sixteen- or seventeen-gauge needles are most commonly used for blood donation, as they are large enough to allow red blood cells to pass through the needle without rupturing (this also allows more blood to be collected in a shorter time). Larger-gauge needles (with smaller diameter) will rupture the red blood cells, and if this occurs, the blood is useless for the patient receiving it.

The needle (N) is advantageously sterile and apyrogenic. For this purpose, it is profitably manufactured, then packed in an original pack under sterile and apyrogenic conditions. It is preferably kept sterile and apyrogenic in the original pack until it is used, and it is further preferably used one and only one time.

Figure 2:
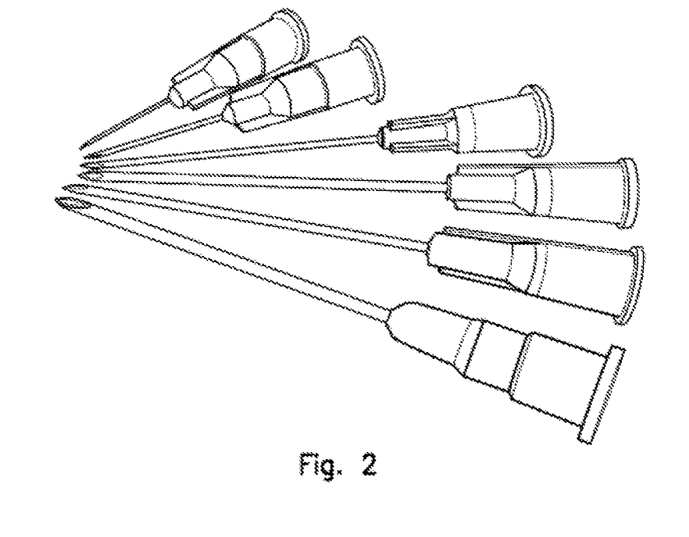
FIG. 2 illustrate several embodiments in which a needle is embedded in a hub that is attached to the barrel of syringe.

The needle (N) is advantageously a disposable needle. The needle (N), especially when it is disposable, is commonly embedded in a hub that is attached to the barrel of a syringe, typically by means of a press-fit or twist-on fitting, and is then commonly referred to as a "Luer Lock" connection, as shown in FIG. 2;

The hub can be composed of aluminum, of a plastic material other than the polyarylene material (M) such as a polyetheretherketone or a wholly aromatic polyester; preferably, the hub is essentially free or is free of metal; very preferably, the hub is composed of a polyarylene material (M') comprising at least one polyarylene (P), said polyarylene material (M') being identical to or different from the polyarylene material (M).

Hence, another aspect of the invention is directed to a hub capable of being attached to the barrel of a syringe, wherein the needle (N) is embedded in the hub and the hub comprises or is composed of the polyarylene material (M') as previously defined. Related aspects of the invention are directed (i) to a needle system comprising a hub capable of being attached to the barrel of a syringe and of the needle (N) embedded in said hub, wherein the hub comprises or consists of the polyarylene material (M') as previously defined, and (ii) to a needle system consisting of a hub capable of being attached to the barrel of a syringe and of the needle (N) embedded in said hub, wherein the hub comprises or consists of the polyarylene material (M') as previously defined.

Still another aspect of the present invention is directed to a draining or administering cannula-based system comprising a cannula having a lumen and a trocar positioned in the lumen at one extremity of the cannula, wherein the trocar is the needle (N) as above described. A cannula is a usually flexible tube, designed to be inserted into a bodily cavity, duct, or vessel to drain fluid or administer a substance such as a medication, while a trocar is a sharp-pointed surgical instrument, designed to be used with a cannula to puncture a body cavity, duct or vessel for fluid aspiration. Preferably, the cannula is composed of a polyarylene material (M") comprising at least one polyarylene (P), said polyarylene material (M") being identical to or different from the polyarylene material (M).

Still another aspect of the present invention is directed to an injection syringe comprising a piston, a pump body equipped with an end fitting for fitting of an injection needle, and an injection needle, wherein the injection needle is the needle (N) as above described. The body of the injection needle has generally a hollow section all along its longitudinal axis. Preferably, the pump body equipped with its end-fitting and the piston are composed of a polyarylene material (M'") comprising at least one polyarylene (P), said polyarylene material (M'") being identical to or different from the polyarylene material (M).

Still another aspect of the present invention is directed to a recipient connector comprising a first hollow section suitable for fitting around neck of a first recipient, a second hollow section suitable for fitting around neck of a second recipient, the first hollow section and the second hollow section being separated from each other by a horizontal wall and a means of perforation of elastic capsules of the first and second recipients, wherein the means of perforation is the needle as above described, which is located at the center of the horizontal wall and the body of which is beveled at both ends.

It is of course possible to build various kinds and designs for the needle (N) according to the present invention, including those shown on the above last photograph.

The needle (N) can be manufactured using commonly known techniques to the skilled in the art for melt processing the polyarylene materials (M), (M'), (M") and (M'"), including extrusion, injection molding, compression molding and solution casting. The needle (N) can be notably manufactured using any method, or any step of a method described in any of the documents that have herein incorporated by reference. Reference can also be made to the "PrimoSpire® PR-250 SRP Injection Molding Guidelines" and to the "PrimoSpire® Self-Reinforced Polyphenylene (SRP) Machining Guidelines" brochures, made available by SOLVAY ADVANCED POLYMERS, L.L.C., the whole content of which is also herein incorporated by reference.

Hence, another aspect of the present invention is directed to a method of manufacturing the needle (N), which comprises melt processing, e.g. extruding, the polyarylene material (M).

Still another aspect of the present invention relates to the use of the needle (N) for any of the above described uses for which it has been designed, or to the use of the needle (N) in a medical, surgical or cosmetic application; the so-used needle is advantageously sterile and apyrogenic. In particular, the present invention relates to the use of the needle (N) for therapeutically or surgically treating a human or animal patient. This includes, for example, the use of the needle (N) as hypodermic needle, i.e. to introduce or remove a material subcutaneously from a human or animal body.

Still another aspect of the present invention relates to the disposal, e.g. by incineration, of the needle (N) after it has been used one and only one time.

A last aspect of the present invention relates to a process for recycling the needle (N) as above described or the needle (N) used in accordance with any of the above described uses, which comprises:

(i) contacting the needle (N) with a solvent of the polyarylene (P) so as to dissolve at least the polyarylene (P) in the solvent;
(ii) causing at least the dissolved polyarylene (P) to precipitate from the solvent e.g. by the addition of an anti-solvent; then
(iii) recovering the precipitated polyarylene (P) or a polyarylene material comprising the precipitated polyarylene (P) e.g. in the form of powder or granules.

Examples of solvents of the polyarylene (P) suitable for use in the present recycling process are described notably in the present specification, and include e.g. N-methylpyrrolidinone. Examples of anti-solvents of the polyarylene (P) suitable for use in the present recycling process are also described in the present specification, and include e.g. isopropanol.

The recycling process may further comprise the step, subsequent to step (iii), of (iv) manufacturing a shaped article from the recovered polyarylene (P) or from a polyarylene material comprising the precipitated polyarylene (P).

Obviously, the present recycling process is also useful, and can thus also be used, for recycling any shaped article other than the needle (N), provided the shaped article of concern comprises a polyarylene material (M) comprising a polyarylene (P), as the needle (N) does.

The Polyarylene Materials (M), (M'), (M") and (M'")

As herein used, the term "polyarylene material" denotes indifferently a single polyarylene (P), a polyarylene blend consisting of two or more polyarylenes (P), or a polyarylene composition comprising at least one polyarylene (P) and at least one other polymeric or non polymeric ingredient other than the polyarylene (P).

The Polyarylene (P)

For the purpose of the present invention, an arylene group is a hydrocarbon divalent group consisting of one core composed of one benzenic ring or of a plurality of benzenic rings fused together by sharing two or more neighboring ring carbon atoms, and of two ends.

Non limitative examples of arylene groups are phenylenes, naphthylenes, anthrylenes, phenanthrylenes, tetracenylenes, triphenylylenes, pyrenylenes, and perylenylenes. The arylene groups (especially the numbering of the ring carbon atoms) were named in accordance with the recommendations of the CRC Handbook of Chemistry and Physics, 64$^{th}$ edition, pages C1-C44, especially p. C11-C12.

Arylene groups present usually a certain level of aromaticity; for this reason, they are often reported as "aromatic" groups. The level of aromaticity of the arylene groups depends on the nature of the arylene group; as thoroughly explained in Chem. Rev. 2003, 103, 3449-3605, "Aromaticity of Polycyclic Conjugated Hydrocarbons", the level of aromaticity of a polycyclic aromatic hydrocarbon can be notably quantified by the "index of benzene character" B, as defined on p. 3531 of the same paper; values of B for a large set of polycyclic aromatic hydrocarbon are reported on table 40, same page.

An end of an arylene group is a free electron of a carbon atom contained in a (or the) benzenic ring of the arylene group, wherein an hydrogen atom linked to said carbon atom has been removed. Each end of an arylene group is capable of forming a linkage with another chemical group. An end of an arylene group, or more precisely the linkage capable of being formed by said end, can be characterized by a direction and by a sense; to the purpose of the present invention, the sense of the end of an arylene group is defined as going from the inside of the core of the arylene group to the outside of said core. As concerns more precisely arylene groups the ends of which have the same direction, such ends can be either of the same or opposite sense; also, their ends can be in the straight foregoing of each other, or not (otherwise said, they can be disjoint).

A polyarylene is intended to denote a polymer, other than a poly(aryl ether ketone) as defined below, of which more than 25 wt. % of the recurring units are recurring units (R) of one or more formulae consisting of an optionally substituted arylene group, provided said optionally substituted arylene group is linked by each of its two ends to two other optionally substituted arylene groups via a direct C—C linkage. That the optionally substituted arylene group is linked by each of its two ends to two other optionally substituted arylene groups via a direct C—C linkage, is an essential feature of the recurring units (R); thus, an arylene recurring unit which is linked by at least one of its two ends to a group other than an arylene group such as phenylene recurring units $\varphi_1$, $\varphi_2$ and $\varphi_{2'}$, such as:
—O-$\varphi_1$-S(═O)$_2$— or
—O-$\varphi_2$-$\varphi_{2'}$-O—
is not a recurring unit (R) in the sense of the present invention.

The arylene groups of which the recurring units (R) consist can be unsubstituted. Alternatively, they can be substituted by at least one monovalent substituting group.

The monovalent substituting group is usually not polymeric in nature; its molecular weight is preferably below 500, more preferably below 300, still more preferably below 200 and most preferably below 150.

The monovalent substituting group is advantageously a solubilizing group. A solubilizing group is one increasing the solubility of the polyarylene (P) in at least one organic solvent, in particular in at least one of dimethylformamide, N-methylpyrrolidinone, hexamethylphosphoric triamide, benzene, tetrahydrofuran and dimethoxyethane, which can be used as solvents during the synthesis of the polyarylene (P) by a solution polymerization process.

The monovalent substituting group is also advantageously a group which increases the fusibility of the polyarylene (P), i.e. it lowers its glass transition temperature and its melt viscosity, so as to desirably make the polyarylene (P) suitable for thermoprocessing.

Preferably, the monovalent substituting group is chosen from:
hydrocarbyls such as alkyls, aryls, alkylaryls and aralkyls;
halogenos such as —Cl, —Br, —F and —I;
hydrocarbyl groups partially or completely substituted by at least one halogen atom such as halogenoalkyls, halogenoaryls, halogenoalkylaryls and halogenoaralkyls;
hydroxyl;
hydrocarbyl groups substituted by at least one hydroxyl group, such as hydroxyalkyls, hydroxyaryls, hydroxyalkylaryls and hydroxyaralkyls;
hydrocarbyloxys [—O—R, where R is a hydrocarbyl group], such as alkoxys, aryloxys, alkylaryloxys and aralkyloxys;
amino (—NH$_2$);
hydrocarbyl groups substituted by at least one amino group, such as aminoalkyls and aminoaryls;
hydrocarbylamines [—NHR or —NR$_2$, where R is a hydrocarbyl group] such as alkylamines and arylamines;
carboxylic acids and their metal or ammonium salts, carboxylic acid halides, carboxylic anhydrides;
hydrocarbyl groups substituted by at least one of carboxylic acids, metals or ammonium salts thereof, carboxylic acid halides and carboxylic anhydrides, such as —R—C(═O)OH where R is an alkyl or an aryl group;
hydrocarbylesters [—C(═O)OR or —O—C(═O)R, where R is a hydrocarbyl group] such as alkylesters, arylesters, alkylarylesters and aralkylesters;
amido [—C(═O)NH$_2$];
hydrocarbyl groups substituted by at least one amido group;
hydrocarbylamide monoesters [—C(═O)NHR or —NH—C(═O)—R, where R is a hydrocarbyl group], such as alkylamides, arylamides, alkylarylamides and aralkylamides, and hydrocarbylamide diesters [—C(═O)NR$_2$ or —N—C(═O)R$_2$, where R are a hydrocarbyl groups], such as dialkylamides and diarylamides;
sulfinic acid (—SO$_2$H), sulfonic acid (—SO$_3$H), their metal or ammonium salts,
hydrocarbylsulfones [—S(═O)$_2$—R, where R is the hydrocarbyl group], such as alkylsulfones, arylsulfones, alkylarylsulfones, aralkylsulfones;
aldehyde [—C(═O)H] and haloformyls [—C(═O)X, wherein X is a halogen atom];
hydrocarbylketones [—C(═O)—R, where R is a hydrocarbyl group], such as alkylketones, arylketones, alkylarylketones and aralkylketones;
hydrocarbyloxyhydrocarbylketones [—C(═O)—R$^1$—O—R$^2$, where R$^1$ is a divalent hydrocarbon group such as an alkylene, an arylene, an alkylarylene or an aralkylene, preferably a C$_1$-C$_{18}$ alkylene, a phenylene, a phenylene group substituted by at least one alkyl group, or an alkylene group substituted by at least one phenyl group; and R$^2$ is a hydrocarbyl group, such as an alkyl, aryl, alkylaryl or aralkyl group], such as alkyloxyalkylketones, alkyloxyarylketones, alkyloxyalkylarylketones, alkyloxyaralkylketones, aryloxyalkylketones, aryloxyarylketones, aryloxyalkylarylketones and aryloxyaralkylketones;

any of the above groups comprising at least one hydrocarbyl group or a divalent hydrocarbon group $R^1$, wherein said hydrocarbyl group or said $R^1$ is itself substituted by at least one of the above listed monovalent substituting groups, e.g. an arylketone —C(=O)—R, where R is an aryl group substituted by one hydroxyl group;

where:
- the hydrocarbyl groups contain preferably from 1 and 30 carbon atoms, more preferably from 1 to 12 carbon atoms and still more preferably from 1 to 6 carbon atoms;
- the alkyl groups contain preferably from 1 to 18 carbon atoms, and more preferably from 1 to 6 carbon atoms; very preferably, they are chosen from methyl, ethyl, n-propyl, isopropyl, n-butyl, isobutyl and tert-butyl;
- the aryl groups are defined as monovalent groups consisting of one end and one core composed of one benzenic ring (such the phenyl group) or of a plurality of benzenic rings directly linked to each other via a carbon-carbon linkage (such as the biphenyl group) or fused together by sharing two or more neighboring ring carbon atoms (such as the naphthyl groups), and wherein the ring carbon atoms are possibly substituted by at least one nitrogen, oxygen or sulfur atom; preferably, in the aryl groups, no ring carbon atom is substituted;
- the aryl groups contain preferably from 6 to 30 carbon atoms; more preferably, they are phenyl groups;
- the alkyl group which is contained in the alkylaryl groups meets the preferences of the alkyl groups as above expressed;
- the aryl group which is contained in the aralkyl groups meets the preferences of the aryl groups as above expressed.

More preferably, the monovalent substituting group is chosen from hydrocarbylketones [—C(=O)—R, where R is a hydrocarbyl group] and hydrocarbyloxyhydrocarbylketones [—C(=O)—$R^1$—O—$R^2$, where $R^1$ is a divalent hydrocarbon group and $R^2$ is a hydrocarbyl group], said hydrocarbylketones and hydrocarbyloxyhydrocarbylketones being unsubstituted or substituted by at least one of the above listed monovalent substituting groups.

Still more preferably, the monovalent substituting group is chosen from arylketones and aryloxyarylketones, said arylketones and aryloxyarylketones being unsubstituted or substituted by at least one of the above listed monovalent substituting groups.

Most preferably, the monovalent substituting group is an (unsubstituted) arylketone, in particular it is phenylketone [—C(=O)-phenyl].

The core of the optionally substituted arylene group of the recurring units (R) is composed of preferably at most 3, more preferably at most 2, and still more preferably at most one benzenic ring. Then, when the core of the optionally substituted arylene group of the recurring units (R) is composed of one benzenic ring, the recurring units (R) are of one or more formulae consisting of an optionally substituted phenylene group, provided said optionally substituted phenylene group is linked by each of its two ends to two other optionally substituted arylene groups via a direct C—C linkage.

As above explained, the optionally substituted arylene group of the recurring units (R) is linked by each of its two ends to two other optionally substituted arylene groups via a direct C—C linkage. Preferably, it is linked by each of its two ends to two other optionally substituted phenylene groups via a direct C—C linkage.

As also above explained, both ends of the optionally substituted arylene group of the recurring units (R) can be characterized notably by a direction and by a sense.

A first set of recurring units suitable as recurring units (R) is composed of optionally substituted arylene groups, the ends of which
- have the same direction,
- are of opposite sense, and
- are in the straight foregoing of each other
[hereafter, recurring units (R-a)].

Non limitative examples of such optionally substituted arylene groups include:

1,4-phenylene
(also named
p-phenylene)

1,4-naphthylene

1,4-phenanthrylene and
2,7-phenanthrylene and

1,4-anthrylene and
9,10-anthrylene and

2,7-pyrenylene

1,4-naphthacenylene and
5,12-naphthacenylene and

1,4-chrysenylene

1,4-triphenylylene and
2,7-triphenylylene and

1,4-pentacenylene,
5,14-pentacenylene and
6,13-pentacenylene

, and 1,6-coronenylene and any of these groups substituted by at least one monovalent substituting group, as above defined, in particular by a phenylketone group.

Good results are obtained when recurring units (R-a) are optionally substituted p-phenylenes.

Recurring units (R-a), when contained in the polyarylene (P), result in straight polymer chains exhibiting an outstanding rigidity. For this reason, such polyarylenes (P) are commonly referred to as "rigid-rod polymers".

A second set of recurring units suitable as recurring (R) is composed of optionally substituted arylene groups, the ends of which
- either have a different direction, forming thus together an angle between 0 and 180°, said angle being possibly acute or obtuse,
- or have the same direction and the same sense,
- or have the same direction, are of opposite sense and are disjoint (i.e. not in the straight foregoing of each other)

[globally hereafter referred to as recurring units (R-b)].

Then, a first subset of recurring units (R-b) suitable as recurring units (R) is composed of optionally substituted arylene groups, the ends of which have a different direction, forming together an acute angle [recurring units (R-b1)]. Non limitative examples of optionally substituted arylene groups the ends of which have a direction different from each other, include:

1,2-phenylene (or o-phenylene)

1,2-, 2,3- and 1,7-naphtylenes

, and

1,2-, 1,8-, 1,9-, 2,3-, 2,5- and 2,10-phenanthrylenes

,

,

, and 1,2- and 1,7-anthrylenes and and any of these groups substituted by at least one monovalent substituting group, as above defined, in particular by a phenylketone group.

A second subset of recurring units (R-b) suitable as recurring units (R) is composed of optionally substituted arylene groups, the ends of which have a different direction, forming together an obtuse angle [recurring units (R-b2)]. Non limitative examples of optionally substituted arylene groups the ends of which have a direction different from each other, include:

| | |
|---|---|
| 1,3-phenylene (or m-phenylene) |  |
| 1,3- and 1,6-naphthylenes |  and  |
| 1,3-, 1,5-, 1,7-, 2,4-, 2,9- and 3,10- phenanthrylenes |  ,  ,  ,  ,  and  |
| 1,3- and 1,6-anthrylenes |  and  | and any of these groups substituted by at least one monovalent substituting group, as above defined, in particular by a phenylketone group.

A third subset of recurring units (R-b) is composed of optionally substituted arylene groups, the ends of which have the same direction and the same sense [recurring units (R-b3)]. Non limitative examples of optionally substituted arylene groups the ends of which the same direction and the same sense include:

| | |
|---|---|
| 1,8-naphthylene |  |

1,10- and 3,5-phenanthrylenes and

1,8- and 1,9-anthrylenes and

1,6-, 3,9- and 4,10-phenanthrylenes

, and

1,5-, 1,10- and 2,6-anthrylenes

, and and any of these groups substituted by at least one monovalent substituting group, as above defined, in particular by a phenylketone group.

A fourth subset of recurring units (R-b) is composed of optionally substituted arylene groups, the ends of which have the same direction, are of opposite sense and are disjoint [recurring units (R-b4)]. Non limitative examples of such optionally substituted arylene groups include:

1,5- and 2,6-naphthylenes and and any of these groups substituted by at least one monovalent substituting group, as above defined, in particular by a phenylketone group. Preferably, recurring units (R-b) are chosen from recurring units (R-b1), recurring units (R-b2) and recurring units (R-b4). More preferably, recurring units (R-b) are chosen from recurring units (R-b1) and recurring units (R-b2). Still more preferably, recurring units (R-b) are chosen from recurring units (R-b1). Good results are obtained when recurring units (R-b) are optionally substituted m-phenylenes.

Recurring units (R-b), when contained in the polyarylene (P), result in more or less kinked polymer chains, exhibiting a higher solubility and fusibility than straight polymer chains. For this reason, such polyarylenes (P) are commonly referred to as "kinked polymers".

Recurring units (R) are preferably chosen from:
recurring units (R-a) which are substituted by at least one monovalent substituting group [choice (A)]; and
mixes of recurring units (R-a), which can be substituted or not by at least one monovalent substituting group, with recurring units (R-b), which can be substituted or not by at least one monovalent substituting group [choice (B)].

Choice (B) is generally more preferred than choice A.

Choice (A)

Recurring units of choice (A) are recurring units (R-a) which are substituted by at least one monovalent substituting group.

Said recurring units are preferably p-phenylenes substituted by at least one monovalent substituting group.

Very preferably, they are p-phenylenes substituted by at least one monovalent substituting group chosen from hydrocarbylketones [—C(=O)—R, where R is a hydrocarbyl group] and hydrocarbyloxyhydrocarbylketones [—C(=O)—$R^1$—O—$R^2$, where $R^1$ is a divalent hydrocarbon group and $R^2$ is a hydrocarbyl group], said hydrocarbylketones and hydrocarbyloxyhydrocarbylketones being themselves unsubstituted or substituted by at least one monovalent substituting group as those above listed.

Still more preferably, they are p-phenylenes substituted by at least one monovalent substituting group chosen from arylketones and aryloxyarylketones, said arylketones and aryloxyarylketones being unsubstituted or substituted by at least one monovalent substituting group as those above listed.

Most preferably, they are p-phenylenes substituted by an arylketone group, in particular by the phenylketone group.

Choice (B)

Recurring units of choice (B) are a mix of recurring units (R-a), which can be substituted or not by at least one monovalent substituting group, with recurring units (R-b), which can be substituted or not by at least one monovalent substituting group. When such a mix of recurring units is contained in the polyarylene (P), said polyarylene (P) is commonly referred to as "a kinked rigid-rod polymer".

The recurring units of choice (B) are preferably a mix (M) of recurring units (R-a) chosen from optionally substituted p-phenylenes, with recurring units (R-b) chosen from (i) optionally substituted m-phenylenes and (ii) mixes of optionally substituted m-phenylenes with optionally substituted o-phenylenes.

The recurring units (R-a) of the mix (µ) are preferably p-phenylene units substituted by at least one substituting group. More preferably, the recurring units (R-a) of the mix (µ) are p-phenylenes substituted by at least one monovalent substituting group chosen from hydrocarbylketones [—C(=O)—R, where R is a hydrocarbyl group] and hydrocarbyloxyhydrocarbylketones [—C(=O)—$R^1$—O—$R^2$, where $R^1$ is a divalent hydrocarbon group and $R^2$ is a hydrocarbyl group], said hydrocarbylketones and hydrocarbyloxyhydrocarbylketones being themselves unsubstituted or substituted by at least one monovalent substituting group as those above listed. Still more preferably, the recurring units (R-a) of the mix (µ) are p-phenylenes substituted by at least one monovalent substituting group chosen from arylketones and aryloxyarylketones, said arylketones and aryloxyarylketones being unsubstituted or substituted by at least one monovalent substituting group as those above listed. Most preferably, they are p-phenylenes substituted by an arylketone group, in particular by the phenylketone group.

Essentially all, if not all, the recurring units (R-b) of the mix (µ) are m-phenylene units optionally substituted by at least one substituting group. More preferably, essentially all, if not all, the recurring units (R-b) of the mix (µ) are m-phenylene units which are optionally substituted by at least one monovalent substituting group chosen from hydrocarbylketones [—C(=O)—R, where R is a hydrocarbyl group] and hydrocarbyloxyhydrocarbylketones [—C(=O)—$R^1$—O—$R^2$, where $R^1$ is a divalent hydrocarbon group and $R^2$ is a hydrocarbyl group], said hydrocarbylketones and hydrocarbyloxyhydrocarbylketones being themselves unsubstituted or substituted by at least one monovalent substituting group as those above listed. Still more preferably, essentially all, if not all, the recurring units (R-b) of the mix (µ) are unsubstituted m-phenylene units. Most preferably, all the recurring units (R-b) are m-phenylene units.

In the mix (µ), the mole ratio of the recurring units (R-b), based on the total number of moles of the recurring units (R-a) and (R-b), is usually of at least 1%, preferably at least 5%, more preferably at least 20%, still more preferably at least 30% and most preferably at least 40%. On the other hand, in the mix (µ), the mole ratio of the recurring units (R-b), based on the total number of moles of the recurring units (R-a) and (R-b), is usually of at most 99%, preferably at most 95%, more preferably at most 80%, still more preferably at most 70% and most preferably at most 60%.

Good results are obtained when the recurring units of choice (B) are a mix of p-phenylene substituted by a phenylketone group with unsubstituted m-phenylene, in a mole ratio of about 50:50.

The polyarylene (P) may be notably a homopolymer, a random, alternating or block copolymer.

Optionally, the polyarylene (P) may further comprise recurring units (R*), different from recurring units (R).

Recurring units (R*) may contain or not at least one strong divalent electron withdrawing group linked on each of its ends to an arylene group. Non limitative examples of recurring units (R*) free of such strong divalent electron withdrawing group are:

and (1)

(2)

Recurring units (R*) contain preferably at least one strong divalent electron withdrawing group linked on each of its ends to an arylene group, in particular a p-phenylene group. The divalent electron withdrawing group is preferably chosen from the sulfone group [—S(=O)$_2$—], the carbonyl group [—C(=O)—], the vinylene group [—CH=CH—], the sulfoxide group [—S(=O)—], the azo group [—N=N—], saturated fluorocarbon groups like —C(CF$_3$)$_2$—, organic phosphine oxide groups [—P(=O)(=R$_h$)—, where R$_h$ is a hydrocarbyl group] and the ethylidene group [—C(=CA$_2$)—, where A can be hydrogen or halogen]. More preferably, the divalent electron withdrawing group is chosen from the sulfone group and the carbonyl group. Still more preferably, recurring units (R*) are chosen from:

(i) recurring units of formula (3)

(ii) recurring units of formula (4)

wherein Q is a group chosen from with R being:

, with n being an integer from 1 to 6 and n' being an integer from 2 to 6, Q being preferably chosen from and

, (iii) recurring units of formula (5)

(iv) recurring units of formula (6)

Preferably more than 25 wt. %, more preferably more than 50 wt. %, and still more preferably more than 90 wt. % of the recurring units of the polyarylene (P) are recurring units (R). Most preferably, essentially all, if not all, the recurring units of the polyarylene (P) are recurring units (R).

The polyarylene (P) has usually a number average molecular weight greater than 1000, preferably greater than 5000, more preferably greater than about 10000 and still more preferably greater than 15000. On the other hand, the number average molecular weight of the polyarylene (P) is usually below 100000, and preferably below 70000. In a certain embodiment, the number average molecular weight of the polyarylene (P) is above 35000. In another embodiment, it is of at most 35000; in this embodiment, it is often of at most 25000 and sometimes of at most 20000. The number average molecular weight of a polyarylene, in particular that of the polyarylene (P), is advantageously determined by: (1) measuring a "relative" number average molecular weight of the polyarylene by Gel Permeation Chromatography (GPC) using polystyrene calibration standards, then (2) dividing the so-measured "relative" number average molecular weight by a factor 2. It is proceeded accordingly because the skilled in the art who is a specialist of polyarylenes knows that their "relative" number average molecular weight, as measured by GPC, are generally off by a factor of about 2 times; it has already been accounted for this correction factor in all the above cited lower and upper limits of molecular weight.

The polyarylene (P) can be amorphous (i.e. it has no melting point) or semi-crystalline (i.e. it has a melting point). It is preferably amorphous.

The polyarylene (P) has a glass transition temperature of advantageously above 50° C., preferably above 120° C. and more preferably above 150° C.

The polyarylene (P) is generally in a form other than fibers.

The polyarylene (P) can be prepared by any method. Methods well known in the art to prepare the polyarylene (P) are described notably in U.S. Pat. Nos. 5,227,457; 5,539,048; 5,565,543; 5,646,231; 5,654,392; 5,659,005; 5,668,245; 5,670,564; 5,721,335; 5,756,581; 5,760,131; 5,824,744; 5,827,927; 5,869,592; 5,886,130; and 6,087,467, the whole content of which is incorporated herein by reference for all purposes. A suitable method for preparing the polyarylene (P) comprises polymerizing, preferably by reductive coupling, at least one dihaloarylene molecular compound consisting of one optionally substituted arylene group, which is linked on each of its two ends to one halogen atom, such as chlorine, bromine and iodine. The elimination of both halogen atoms from a dihaloarylene molecular compound results in the formation of an optionally substituted arylene group, suitable as a recurring unit (R) of the polyarylene (P).

Thus, for example:
the elimination of both chlorine atoms from one molecule of p-dichlorobenzene, p-dichlorobiphenyl and their homologous of general formula Cl—($\varphi$)$_N$—Cl, N being an integer from 3 to 10, results in the formation of respectively 1, 2 or N adjacent p-phenylene units; thus, p-dichlorobenzene, p-dichlorobiphenyl and their homologous of general formula Cl—($\varphi$)$_N$—Cl, N as above defined, can be polymerized, so as to form p-phenylene units;

2,5-dichlorobenzophenone (p-dichlorobenzophenone) can be polymerized, so as to form 1,4-(benzoylphenylene) units;

2,5-dichloro-4'-phenoxybenzophenone can be polymerized, so as to form 1,4-(4'-phenoxybenzoylphenylene) units;

m-dichlorobenzene can be polymerized, so as to form m-phenylene units.

The polyarylene (P) is a preferably a high purity polyarylene. Typical polyarylene contaminants are Ni, Zn and P. The polyarylene (P) contains advantageously less than 10 ppm of Ni, preferably less than 5 ppm, and more preferably less than 2 ppm Ni. The polyarylene (P) contains advantageously less than 200 ppm of Zn, preferably less than 100 ppm, and more preferably less than 50 ppm Zn. The polyarylene (P) contain advantageously less than 1000 ppm of P, and preferably less than 500 ppm P. When high purity polyarylenes are desired, the mixture obtained after standard polymerization is preferably treated as follows: the reaction mixture is then precipitated in an anti-solvent and then the polymer is isolated; the polymer is then washed multiple times with the anti-solvent to extract the residual dissolved catalysts which are converted to the metal salts which are soluble in the anti-solvent. Examples of anti-solvents are ethanol, propanol, 2-butanone, acetone, methanol, isopropanol and mixtures thereof. Mixtures of these anti-solvents with water or acidic aqueous solutions gave also good results. Excellent results were obtained using acetone, methanol, isopropanol as anti-solvents.

In a preferred embodiment of the present invention, the polyarylene (P) is a certain kinked rigid-rod polyarylene of which more than 50 wt. % of the recurring units (preferably more than 90 wt. % of the recurring units, more preferably essentially all the recurring units, and still more preferably all the recurring units) are recurring units (R) of one or more formulae consisting of an optionally substituted arylene group, provided said optionally substituted arylene group is linked by each of its two ends to two other optionally substituted arylene groups via a direct C—C linkage, said recurring units (R) being a mix ($\mu$) consisting of:
from 5 to 95 mole %, based on the total number of moles of the recurring units (R), of rigid rod-forming arylene units (R-a), said rigid rod-forming arylene units (R-a) being optionally substituted by at least one monovalent substituting group,
with
from 95 to 5 mole %, based on the total number of moles of the recurring units (R), of kink-forming arylene units (Rb), said kink-forming arylene units (Rb) being optionally substituted by at least one monovalent substituting group.

A much preferred polyarylene (P) is the above kinked rigid-rod polyarylene, of which more than 50 wt. % of the recurring units (preferably more than 90 wt. % of the recurring units, more preferably essentially all the recurring units, and still more preferably all the recurring units) are recurring units (R), said recurring units (R) being a mix ($\mu$) consisting of:
from 5 to 95 mole %, based on the total number of moles of recurring units (R), of rigid rod-forming arylene units (R-a) chosen from p-phenylenes optionally substituted by at least one monovalent substituting group,
with
from 95 to 5 mole %, based on the total number of moles of recurring units (R), of kink-forming arylene units (R-b) chosen from m-phenylenes optionally substituted by at least one monovalent substituting group.

A very much preferred polyarylene (P) is the above kinked rigid-rod polyarylene, of which more than 50 wt. % of the recurring units (preferably more than 90 wt. % of the recurring units, more preferably essentially all the recurring units, and still more preferably all the recurring units) are recurring units (R), said recurring units (R) being a mix ($\mu$) consisting of:
from 25 to 75 mole %, based on the total number of moles of recurring units (R), of rigid rod-forming arylene units (R-a) chosen from p-phenylenes optionally substituted by at least one monovalent substituting group,
with
from 75 to 25 mole %, based on the total number of moles of recurring units (R), of kink-forming arylene units (R-b) chosen from m-phenylenes optionally substituted by at least one monovalent substituting group.

Good results are notably obtained when the polyarylene (P) is a polyphenylene copolymer, essentially all, if not all, the recurring units of which consisted of a mix of p-phenylene substituted by a phenylketone group with unsubstituted m-phenylene in a mole ratio p-phenylene:m-phenylene of from 75:25 to 99.0:1.0, preferably of from 79:21 to 95:5, more preferably of from 82:18 to 90:10, and still more preferably of about 85:15. Such a kinked rigid-rod polyphenylene copolymer is commercially available from Solvay Advanced Polymers, L.L.C. as PRIMOSPIRE® PR-120 polyphenylene.

Excellent results are notably obtained when the polyarylene (P) is a polyphenylene copolymer, essentially all, if not all, the recurring units of which consisted of a mix of p-phenylene substituted by a phenylketone group with unsubstituted m-phenylene in a mole ratio p-phenylene:m-phenylene of from 5:95 to 95:5, preferably of from 70:30 to 30:70, more preferably of from 60:40 to 40:60, and still more preferably of about 50:50. Such a polyphenylene copolymer is commercially available from Solvay Advanced Polymers, L.L.C. as PRIMOSPIRE® PR-250, PRIMOSPIRE® PR-9250 or PRONIVA™ polyphenylene. PRIMOSPIRE® PR-9250 and PRONIVA™ polyphenylenes are particularly suitable for medical applications such as needles, as they are manufactured by carefully validated processes, are subject to enhanced controls to provide product traceability, and are tested in an accredited labs.

The polymer material (M) can comprise one and only one polyarylene (P). Alternatively, it can comprise two, three, or even more than three polyarylenes (P).

Optional Ingredients of the Polyarylene Material (M)

The polyarylene material (M) may be essentially composed of the polyarylene. The polyarylene material (M) may be composed of the polyarylene.

Alternatively, the polyarylene material (M) may further contain one or more polymers other than the polyarylene (P), and/or one or more non polymeric additives, collectively called optional ingredients. The weight of the optional ingredients, based on the total weight of the material, ranges advantageously from 0 to 75 wt. %, preferably from 0 to 50 wt. %, more preferably from 0 to 25 wt. % and still more preferably from 0 to 10 wt. %, based on the total weight of the polymer material (M). Excellent results are obtained when the material is essentially free, or is even completely free, of said optional ingredients.

The non polymeric additives of concern include notably fibrous reinforcing agents, particulate fillers and nucleating agents such as talc and silica, adhesion promoters, compatibilizers, curing agents, lubricants, metal particles, mold release agents, organic and/or inorganic pigments like $TiO_2$ and carbon black, dyes, flame retardants, smoke-suppressing agents, heat stabilizers, antioxidants, UV absorbers, tougheners such as rubbers, plasticizers, anti-static agents, melt viscosity depressants, and mixtures thereof.

In a first particular embodiment, the polyarylene material (M) further comprises at least one thermoplastic polymer other than a polyarylene, selected from the group consisting of polyamides, polyether block amides, polyimides, polyetherimides, polyamideimides, poly(aryl ether sulfone)s [such as polyphenylsulfones, bisphenol A polysulfones, polyethersulfones, polyetherethersulfones, polyethersulfoneimides and copolymers and mixtures thereof], poly(aryl ether ketone)s [such as polyetherketones, polyetheretherketones, polyetherketoneketones, and copolymers and mixtures thereof], polyarylene ethers [such as polyphenylene ethers and poly(2,6-dimethyl-1,4-phenylene ether)s], polyphenylene sulfides, polybenzimidazoles, polycarbonates, polyesters, polyurethanes, polyolefins, poly(methyl pentene)s, polytetrafluoroethylenes, polyethylenes, polypropylenes, liquid crystalline polymers, halogenated polymers, and copolymers and mixtures thereof.

In this particular embodiment, the polyarylene material (M) preferably further comprises at least one poly(aryl ether ketone) and, optionally in addition, at least one poly(aryl ether sulfone). As such, the polyarylene material (M) can meet any of the characteristics of the blends (B) and (T) described in U.S. patent application Ser. No. 12/061,442, the whole content of which is herein incorporated by reference for all purposes, wherein the blend (B) comprises at least one polyarylene (P1) in a form other than fibers and at least one poly(aryl ether ketone) (P2), and the blend (T) comprises at least one polyarylene (P1), at least one poly(aryl ether ketone) (P2) and at least one poly(aryl ether sulfone) (P3). In particular, the polyarylene material (M) can be a blend (B) as previously described, wherein the poly(aryl ether ketone) (P2) is a polyetheretherketone (PEEK) homopolymer, essentially all the recurring units of which are of formula and wherein:
the weight of the polyarylene (P1), based on the total weight of the polyarylene (P1) and the poly(aryl ether ketone) (P2), can range from 30% to 70%, and
the total weight of the polyarylene (P1) and the poly(aryl ether ketone) (P2), based on the total weight of the blend (B), can be above 80%.

The polyarylene material (M) can be also a blend (T) as previously described, wherein the poly(aryl ether ketone) (P2) is a polyetheretherketone (PEEK) homopolymer, essentially all the recurring units of which are of formula and the poly(aryl ether sulfone) (P3) is a polyphenylsulfone homopolymer (PPSU), essentially all the recurring units of which are of formula and wherein:
the weight of the polyarylene (P1), based on the total weight of the polyarylene (P1) and the poly(aryl ether ketone) (P2), can range from 30% to 70%,
the poly(aryl ether sulfone) (P3) over polyarylene (P1) weight ratio can range from 0.15 to 0.50,
the poly(aryl ether sulfone) (P3) over poly(aryl ether ketone) (P2) weight ratio can range from 0.15 to 0.50, and
the total weight of the polyarylene (P1), the poly(aryl ether ketone) (P2) and the poly(aryl ether sulfone) (P3), based on the total weight of the blend (T), can be above 95%.

In another particular embodiment, the polyarylene material (M) comprises
at least one polyarylene (P4), of which the efficient arylene recurring units (R1) are a mix (M1) consisting of:
from 70 mole % to 100 mole %, based on the total number of moles of efficient arylene recurring units (R1), of rigid rod-forming arylene units (Ra), said rigid rod-forming arylene units (Ra) being optionally substituted by at least one monovalent substituting group
with
from 0 to 30 mole %, based on the total number of moles of efficient arylene recurring units (R1), of kink-forming arylene units (Rb), said kink-forming arylene units being optionally substituted by at least one monovalent substituting group,
and
at least one polyarylene (P5), of which the efficient arylene recurring units (R2) are a mix (M2) consisting of:
less than 70 mole %, down to 0 mole %, based on the total number of moles of efficient arylene recurring units (R2), of rigid rod-forming arylene units (Ra), said rigid rod-forming arylene units (Ra) being optionally substituted by at least one monovalent substituting group with
more than 30 mole %, up to 100 mole %, based on the total number of moles of efficient arylene recurring units (R2), of kink-forming arylene units (Rb), said kink-forming arylene units being optionally substituted by at least one monovalent substituting group.

In a further particular embodiment the polyarylene material (M) comprises, the above described polyarylene (P4) and (P5), a poly(aryl ether ketone) (P2) and optionally in addition a poly(aryl ether sulfone) (P3). In this embodiment, the poly(aryl ether ketone) (P2) is preferably a polyetheretherketone (PEEK) homopolymer, essentially all the recurring units of which are of formula and the poly(aryl ether sulfone) (P3) is a polyphenylsulfone homopolymer (PPSU), essentially all the recurring units of which are of formula In another particular embodiment, to which the preference is generally not given, the polymer material (M) further contains at least one fibrous reinforcing agent, in particular an inorganic fibrous reinforcing agent such as glass fiber or carbon fiber, usually in an amount of from 10 to 50 wt. %, based on the total weight of the polymer material (M). This embodiment is generally not preferred because the neat polyarylene (P) has generally a high enough flexural and compression strength, and a high enough rigidity, and because the fibrous reinforcing agent generally impairs the ductility of the polyarylene material (M).

The needle (N) of the present invention presents lots of unexpected advantages.

It meets advantageously a confluence of characteristics including high compression and flexural strength, high rigidity, high stiffness, high surface hardness, high ductility, high impact resistance, high chemical resistance, high corrosion resistance, non combustibility, low moisture absorption.

The needle (N) has advantageously not just a good, but an excellent penetrability.

The needle (N) excels advantageously in its ability to hold a sharp edge. It can even be able to hold an extremely sharp edge.

The needle (N) is advantageously non toxic, non irritant. The needle (N) can even have all the attributes of a biocompatible material.

The needle (N) is advantageously easily disposable needles, hence especially well suited for a single-use. The needle (N) cannot just be easily disposed, it can further be recycled to form other shaped articles.

The needle (N) is advantageously made of a thermally stable material, and can be easily obtained by conventional melt processing techniques.

Biocompatibility Test Results

The biocompatibility of a polyarylene copolymer essentially all, if not all, the recurring units of which consisted of a mix of p-phenylene substituted by a phenylketone group with unsubstituted m-phenylene in a mole ratio p-phenylene:m-phenylene of about 50:50, commercially available from Solvay Advanced Polymers, L.L.C. as PRIMOSPIRE® PR-250 polyarylene, was tested using 4 standard tests covering cytotoxicity, sensitization, systemic toxicity and sub-acute (subchronic toxicity).

ISO Guinea Pig Maximization Sensitization Test Results:

Pellets of the polyarylene were extracted according to ISO 10993-12. The resulting extracts and control blanks were injected to different guinea pigs. On day 6, the dorsal site was reshaved and sodium lauryl sulfate in mineral oil was applied. On day 7, the animals were topically patched with the appropriate test extract and the corresponding blank animals were patched with the corresponding control blank. The patches were removed after 48±2 hours of exposure. Following a 2 week rest period, the animals were topically patched with the appropriate test extract and the corresponding blank animals were patched with the corresponding control blank. The patches were removed after 24±2 hours of exposure. The dermal patch sites were observed for erythema and edema 24±2 and 48±2 hours of exposure. Each animal was assessed for a sensitization response based upon the dermal scores. None of them elicit a sensitization response.

Minimum Essential Medium Elution Using L-929 Mouse Fibroblast Cells (ISO) (Cytotoxicity) Test Results:

Pellets of the polyarylene were extracted at 37±1° C. for 24-25 hours. The extract was inoculated onto the cell line and incubated at 37±1° C. in a humidified atmosphere with 5±1% $CO_2$ in the air. Cultures were evaluated for cytotoxic effects by microscopic observations after 24, 48 and 72 hours incubation periods. The polyarylene was considered non-toxic.

ISO Intracutaneous Reactivity Test:

Pellets of the polyarylene were extracted for 72±2 hours at 37±1° C. Two New Zealand white rabbits (*Oryctolagus cuniculus*) each received 5 sequential 0.2 mL intracutaneous injections along either side of the dorsal mid-line with the test extract on one side and the control extract on the other. The irritations reactions were scored at 24, 48 and 72 hours post-injection on each rabbit for evidence of erythema and edema. The polyarylene was considered as non-irritant. ISO Acute Systemic Injection Test Pellets of the polyarylene were extracted for 72±2 hours at 37±2° C. Groups of five albino, Swiss mice (*Mus musculus*) were injected systemically with test or control extracts at a dosing of 50 mL per kg body weight. The animals were observed for signs of toxicity immediately after injection and at 4, 24, 48 and 72 hours post injection. The polyarylene was considered non-toxic.

The invention has been described with reference to various preferred and other embodiments but is not limited thereto. Those skilled in the art will appreciate that various modifications can be made without departing from the scope of the invention, which is defined by the following claims.

The invention claimed is:

1. A needle (N) comprising a body extending along a longitudinal axis and having two ends, wherein at least one end of the body is beveled to form a sharp beveled edge at an angle α ranging from 2.5° to 60°, and wherein the body comprises a polyarylene material (M) comprising at least one polyarylene (P), wherein more than 25 wt. % of the recurring units of the polyarylene (P) are recurring units (R) of one or more formulae consisting of an optionally substituted arylene group, wherein said optionally substituted arylene group is linked by each of its two ends to two other optionally substituted arylene groups via a direct C—C linkage, wherein said recurring units (R) consist of:
- from 5 to 95 mole %, based on the total number of moles of recurring units (R), of rigid rod-forming arylene units (Ra) selected from p-phenylenes optionally substituted by at least one monovalent substituting group, and
- from 95 to 5 mole %, based on the total number of moles of recurring units (R), of kink-forming arylene units (Rb) selected from m-phenylenes optionally substituted by at least one monovalent substituting group.

2. The needle according to claim 1, wherein the body is essentially cylindrical.

3. The needle according to claim 1, wherein the body has a hollow section all along its longitudinal axis.

4. The needle according to claim 3, wherein the hollow section is circular.

5. The needle according to claim 1, wherein the body is beveled at one and only one end to form the sharp beveled edge.

6. The needle according to claim 1, wherein the body is beveled at both ends, and wherein at least one of the ends forms the sharp beveled edge.

7. The needle according to claim 1, wherein the angle a which the longitudinal axis makes with the at least one beveled end ranges from 2.5° to 35°.

8. The needle according to claim 1, wherein the needle is free of reinforcement filaments embedded in the polyarylene material (M).

9. The needle according to claim 1 consisting of the body-being cylindrical, having a circular hollow section all along its longitudinal axis, wherein only one end of the body is beveled to form the sharp beveled edge, and wherein the body being composed of the polyarylene material (M).

10. The needle according to claim 1 is a medical needle for introducing or removing parenterally a material from a human or animal body, or a surgical needle for carrying sutures on a tissue for puncturing a tissue or to passing a ligature on a conduit of a human or animal body.

11. The needle according to claim 1, wherein the polyarylene material (M) is free of fibrous filler.

12. The needle according to claim 1, wherein more than 25 wt. % of the recurring units of the polyarylene (P) are recurring units (R) of one or more formulae consisting of an optionally substituted arylene group, wherein said optionally substituted arylene group is linked by each of its two ends to two other optionally substituted arylene groups via a direct C—C linkage, wherein said recurring units (R) consist of:
- from 25 to 75 mole %, based on the total number of moles of recurring units (R), of rigid rod-forming arylene units (Ra) selected from p-phenylenes optionally substituted by at least one monovalent substituting group, and
- from 75 to 25 mole %, based on the total number of moles of recurring units (R), of kink-forming arylene units (Rb) selected from m-phenylenes optionally substituted by at least one monovalent substituting group.

13. The needle according to claim 1, wherein the polyarylene material (M) further comprises at least one poly(aryl ether ketone).

14. The needle according to claim 1, wherein the polyarylene material (M) is free of optional ingredients selected from the group consisting of polymers other than the polyarylene (P), one or more non-polymeric additives, and combinations thereof.

15. The needle according to claim 1, wherein the angle a ranges from 3.0° to 45°.

16. A process for recycling the needle according to claim 1, the process comprising:
(i) contacting the needle with a solvent of the polyarylene (P) such that the polyarylene (P) dissolves in the solvent to form a solvent and polyarylene (P) mixture;
(ii) adding an anti-solvent to the mixture to precipitate the polyarylene (P) from the mixture; and
(iii) recovering the polyarylene (P) precipitated from the mixture.

* * * * *